(12) United States Patent
Syvret et al.

(10) Patent No.: US 6,270,843 B1
(45) Date of Patent: Aug. 7, 2001

(54) PROCESS FOR GENERATING USEFUL ELECTROPHILES FROM COMMON ANIONS AND THEIR APPLICATION IN ELECTROPHILIC REACTIONS WITH ORGANIC SUBSTRATES

(75) Inventors: Robert George Syvret, Allentown; Tung Phuong Nguyen, Pittsburgh; Victoria Lee Bulleck, Perkasie; Ryan Dennis Rieth, Bethlehem, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/535,756

(22) Filed: Mar. 27, 2000

(51) Int. Cl.$^7$ ....................................................... B05D 1/00
(52) U.S. Cl. ............................................................ 427/384
(58) Field of Search .............................................. 427/384

(56) References Cited

PUBLICATIONS

J. March, *Advanced Organic Chemistry*, Wiley, NY, '85, pp. 447–511.
P.B.D. De La Mare, *Aromatic Substitution*, Butterworths: London, '59.
"Chemical Reviews", G.S. Lal, 1996, 96(5), 1737.
*J. Org. Chem.*, vol. 40, No. 23, '75 pp.3373–3375.
*J. Heterocyclic Chem.*, S.M. Bonesi,., 34, '97, pp. 877–889.
Araki, S.; Butsugan, Y. *Tetrahedron Lett.* '84, 25(4), pp. 441–444.
Goldberg, Y.; Alper, H., *J. Org. Chem.*, '93, 58, pp. 3072–3075.
Lambert, F.L.; Ellis, W.D., Parry, R.J., *J. Org. Chem.*, '65, 30, pp. 304–306.
Cookson, R.F.; Richards, A.C.J., *J. Chem. Soc., Chem. Commun.* '74, pp. 585–586.
Gershon, H.; McNeil, N.W., *J. Org. Chem.*, '72, 37(25), pp. 4078–4082.
Lindsay–Smith, J.R.; McKeer, L.C., *Tetrahedron Lett.* '83, 24(30), pp. 3117–3120.
Lengyel, I.; Cesare, V.; Stephani, R., *Synth. Commun.*, '98, 28(10), pp. 1891–1896.
Hirano, M., Yakabe, S., Monobe, H., Morimoto, T., *Can. J. Chem.*, 75, '97, pp. 1905–1912.
Effenberger, F., Kussmaul, U., Huthmacher, K., *Chem. Ber.*, '79, 112, 1677.
Schlama, T., Gabriel, K., Gouverneur, V., Mioskowski, C., *Angew. Chem. Int. Ed. Engl.*, '97, 36(21), pp. 2342–2344.
Kakinami, S., Moriwaki, M., Tanaka, T., Fujisaki, S., Kakinami, T., Okamoto, T., *J. Chem. Soc., Perkin Trans. 1*, '90, pp. 897–899.
Carreno, M.C., Ruano, G., Sanz, G., Toledo, M., Urbano, A., *Tetrahedron Lett.*, '96, 37(23), pp. 4081–4083.
Olah, G.A., Wang, Q., Sandfrod, G., Prakash, G.K.S., *J. Org. Chem.*, '93, 58, pp. 3194–3195.
Kajigaeshi, S., Kakinami, S., Yamasaki, H., Fujisaki, S., Kondo, M., Okamoto, T., *Chem. Lett.*, '87, pp. 2109–2112.
"New Fluorinating Agents in Organic Synthesis", German, L., Zemskov, S., Eds., Springer–Verlag: Berlin, '89.
Fieser and Fieser in "Reagents for Organic Synthesis", Wiley, NY, vol. 1, '67, pp. 1152–1153.
Tamura, Y., Kwon, S., Chun, M.W., Ikeda, M., *J. Heterocycl. Chem.*, '78, 15, pp. 425–427.
Fieser and Fieser in "Reagents for Organic Synthesis", Wiley, NY, vol. 1, '67, p. 1153.
Angus, A.B., Bacon, R.G.R., *J. Chem. Soc.*, '58, pp. 774–778.
Bacon, R.G.R., Guy, R.G., *J. Chem. Soc.*, '60, pp. 318–324.
Nagamachi, T., Fourrey, J–L., Torrence, P.F., Waters, J.A., Witkop, B., *J. Med. Chem.*, '74, 17(4), pp. 403–406.
Bruno, M., Margarita, R., Parlanti, L., Piancatelli, G., Trifoni, M., *Tetrahedron Lett.*, '98, 39, pp. 3847–3848.
Takagi, K., Takachi, H., Hayama, N., *Chem., Lett.*, '92, pp. 509–510.
Takagi, K., Takachi, H., Sasaki, J., *J. Org. Chem.*, '95, 60, pp. 6552–6556.
Li, A.L., *Chinese Chem. Lett.*, '91, 2(9), pp. 675–676.
Olah, G.A., Kuhn, S.J., Flood, S.H., *J. Am. Chem. Soc.*, '61, 83, pp. 4571–4580.
Olah, G.A., Kuhn, S.J., Flood, S.H., *J. Am. Chem. Soc.*, '61, 83, pp. 4581–4585.
Olah, G.A., Kuhn, S.J., *J. Am. Chem. Soc.*, '62, 84, pp. 3684–3687.
Olah, G.A., Kuhn, S.J., Flood, S.H., Evans, J.C., *J. Am. Chem. Soc.*, '62, 84, p. 3687.
Kuhn, S.J., G.A., *J. Am. Chem. Soc.*, '61, 83, pp. 4564–4571.
Olah, G.A., Lin, H.C., *Synthesis*, '73, pp. 488–489.
Uemura, S., Toshimitsu, A., Okano, M., *J. Chem. Soc., Perkin Trans. I*, '78, pp. 1076–1079.
Zupan, M., Iskra, J., Stavber, S., *Tetrahedron Lett.*, '97, 38(35), pp. 6305–6306.
Gilicinski, A.G., Pez, G.P., Syvret, R.G., Lal, G.S., *J. Fluroine Chem.*, '92, 59, pp. 157–162.

Primary Examiner—Erma Cameron
(74) Attorney, Agent, or Firm—Geoffrey L. Chase

(57) ABSTRACT

A process includes substituting a substituent on a substrate. The process includes reacting a salt of an anionic form of the substituent with an electrophilic fluorination agent to provide an electrophile containing a cationic form of the substituent. The electrophile is then electrophilically substituted on the substrate. In some aspects of the process, the substrate can be an aromatic or a non-aromatic. The process can be used for a variety of reactions having electrophilic mechanisms, including halogenation, thiocyanation and nitration.

21 Claims, No Drawings

PROCESS FOR GENERATING USEFUL ELECTROPHILES FROM COMMON ANIONS AND THEIR APPLICATION IN ELECTROPHILIC REACTIONS WITH ORGANIC SUBSTRATES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to electrophilic reactions and reactants, and more particularly to a process for generating useful electrophiles, $E^+$, from common anions, $E^-$.

Electrophilic addition/substitution of aromatic systems is a field of chemistry that has been widely studied (1–4). Specific examples of reactions having electrophilic mechanisms include halogenation, thiocyanation and nitration.

Reagents for electrophilic halogenation are available in numerous forms ranging from the diatomic element to some fairly exotic halogen delivery reagents (1–5). Most of these reagents are necessarily prepared in advance of halogenation, but some are generated in situ. Reagents specific for electrophilic halogenation include but are not limited to N-chlorosuccinimide (6–12) (NCS), N-chloroammonium salts (13), tert-butylhypochlorite (14), sodium chlorite/(salen)Mn(III) complex (15), chlorine trifluoromethanesulfonate (16), and triethylammonium trichloride (17), for chlorination, N-bromosuccinimide (8–12) and alkylammonium tribromide (18) for bromination, N-iodosuccinimide (19), iodine(I) triflate (20), and dichlorohypoiodite salts (21) for iodination, and various –NF, –XeF, and –OF agents for fluorination (6, 22).

Reagents which are known to deliver electrophilic thiocyanogen include thiocyanogen (23, 24), cyanogen chloride (25–28), and metal thiocyanates mediated by aryliodite (29), NCS (30, 31), and NBS (31, 32).

Electrophilic nitration can be accomplished using a variety of techniques (1). In particular, reagents available include nitronium salts (33–37), methyl nitrate (38), and sodium nitrite mediated by trifluoroacetic acid (39).

Zupan et al. (40) discloses an electrophilic fluorination agent functioning as a mediator in affecting electrophilic reactions. In this reference, mixtures of anisole, Selectfluor™ (i.e., 1-chloromethyl-4-fluoro-1,4-diazoniabicyclo[2.2.2]octane-bis(tetrafluoroborate), hereinafter referred to as F-TEDA-$BF_4$) and $I_2$, KI, $Me_3SiI$, or MeI in solution were shown to produce iodo anisole derivatives regioselectively. This result is not surprising, however, since it has been established that F-TEDA-$BF_4$ readily and immediately oxidizes iodide to iodine in solution (39).

There is a general need for effective methodologies for introducing various functional groups into aromatic systems. In particular, electrophilic methodologies find widespread applications since these reactions are very well understood and the product distribution is generally predictable. Despite the importance of synthetic methods for introducing electrophiles into aromatic systems, relatively few reagents are available to accomplish such transformations, and moreover, the reagents themselves can be difficult to prepare and use.

Accordingly, it would be desirable to provide an easily employed and generally applicable method for introducing electrophilic groups, $E^+$, into a variety of aromatic systems.

All references cited herein are incorporated herein by reference in their entireties.

BRIEF SUMMARY OF THE INVENTION

The present invention provides a process for substituting a substituent on a substrate. The process comprises reacting a salt of an anionic form of the substituent with an electrophilic fluorination agent to provide an electrophile comprising a cationic form of the substituent. The electrophile is then electrophilically substituted on the substrate.

BRIEF DESCRIPTION OF SEVERAL VIEWS OF THE DRAWINGS

Not applicable.

DETAILED DESCRIPTION OF THE INVENTION

The present invention relates to a new process for achieving regioselective electrophilic aromatic substitution of an electrophile, $E^+$, from mixtures of an electrophilic fluorination agent and a salt of the electrophile in a solvent. This process can be described in general terms by Equation 1, below, wherein $F^+$ represents the electrophilic fluorination agent, $M^+X^-$ represents a salt (e.g., an ammonium or sodium salt) of chloride ($Cl^-$), bromide ($Br^-$), thiocyanate ($SCN^-$), nitrite ($NO_2^-$), acetate ($CH_3COO^-$), or trifluoroacetate ($CF_3COO^-$), and $R_{1-6}$ each independently represent a strongly deactivating to strongly activating substituent selected from the group consisting of H, F, Cl, $CH_3$, COOH, $C(O)CH_3$, $NO_2$, OR' and NR'R", where R' and R" are H, $C(O)CH_3$ or $CH_3$.

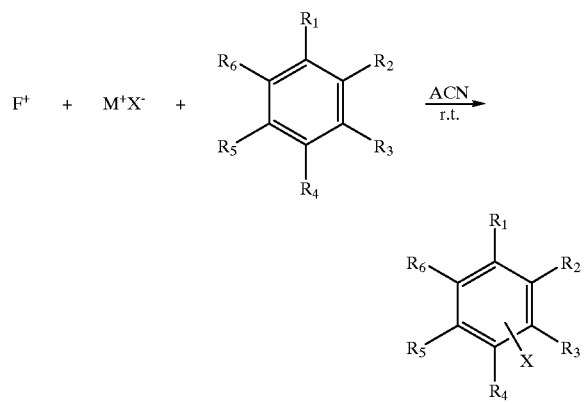

(1)

From this reaction, electrophiles $Cl^+$, $Br^+$, $SCN^+$ and $NO_2^+$ are generated from their respective sodium or ammonium salts by reaction with F-TEDA-$BF_4$ in acetonitrile solution at ambient temperature and pressure. The said generated electrophiles are then reacted directly in situ with various aromatic substrates, including anisole, toluene, p-xylene, phenol, benzene, acetanilide, dimethylaniline, 2-chloro-p-xylene, 2-fluoroanisole, 4-fluoroanisole, 1,3-dimethyluracil, nitrophenol, benzoic acid, or 4'-methoxyacetophenone to give the corresponding addition/substitution products in high yield and purity. In many cases, the yield is quantitative.

In embodiments, the said generated electrophiles can be reacted in situ with any electrophilic addition process, e.g., non-aromatic substrates. Examples of non-armoatic substrates useful in the present invention include 1,3-dimethyluracil and cis-cyclooctene.

The electrophilic fluorination agent is preferably 1-fluoro-4-hydroxy-1,4-diazoniabicyclo[2.2.2]octane-bis(tetrafluoroborate) (hereinafter NFTh). A particularly preferred form of NFTh is Accufluor™ (AlliedSignal Inc., Morristown, N.J.). A particularly preferred electrophilic fluorination agent is 1-chloromethyl-4-fluoro-1,4-diazoniabicyclo[2.2.2]octane-bis(tetrafluoroborate) (hereinafter F-TEDA-BF$_4$). A particularly preferred form of F-TEDA-BF$_4$ is Selectfluor™ (Air Products and Chemicals, Allentown, Pa.).

In embodiments, other bicyclo electrophilic fluorination agents that possess sufficient oxidizing power to effect the transformation of E$^-$ to E$^+$ are suitable for use in this process. For example, 1-fluoro-4-methyl-1,4-diazoniabicyclo[2.2.2]octane-bis(tetrafluoroborate), is a preferred bicyclo electrophilic fluorination agent. A particularly preferred form of 1-fluoro-4-methyl-1,4-diazoniabicyclo[2.2.2]octane-bis(tetrafluoroborate) is Selectfluor(II)™ (Air Products and Chemicals, Allentown, Pa.).

In further embodiments, other N-F fluorination agents are also suitable for use in the present process as electrophilic fluorination agents, for example, N-fluoro-bipyridyl salts, such as N,N'-difluoro-2,2' bipyridinium bis(tetrafluoroborate). A particularly preferred form of N,N'-difluoro-2,2' bipyridinium bis(tetrafluoroborate) is Syn-Fluor™ (SynQuest Laboratories, Inc., Alachua, Fla.).

Although acetonitrile is the most preferred solvent for use in the invention, other nitrile-containing solvents are acceptable, such as, e.g., proprionitrile. Furthermore, amide containing solvents such as, e.g., dimethylformamide (herenafter DMF) could also be used. Solvent mixtures are also suitable, for example in certain embodiments, a mixture of acetonitrile and DMF, or a 50:50 (v/v) mixture of water and acetonitrile is used.

The invention will be illustrated in more detail with reference to the following examples, but it should be understood that the present invention is not deemed to be limited thereto.

EXAMPLE 1
Thiocyanation of Anisole 7.1 g (20 mmol) of F-TEDA-BF$_4$ fluorination agent, 1.6 g (20 mmol) of NaSCN, and 200 mL of acetonitrile were added to a 500-mL round bottom flask containing a magnetic stir bar and stirring was commenced. Anisole was then added in an amount of 2.2 g (20 mmol) and the contents of the flask were stirred under nitrogen and sampled periodically. After 20 hours of stirring at room temperature, analysis by gas chromatography (GC) and gas chromatography—mass spectrometry (GC-MS) indicated that about 67% conversion of the anisole starting material had been achieved with a product distribution of 1% and 62% 2- and 4-methoxyphenylthiocyanate, respectively. At this point, the solvent was removed under vacuum on a Rotavap. To the resulting residue was added 200 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 5% ethyl acetate and 95% hexane. A product fraction was collected, evaporated to a residue, and then analyzed by NMR spectroscopy, GC-MS, and gas chromatography-infrared spectroscopy (GC-IR) and shown to be a mixture of 2- and 4-methoxyphenylthiocyanate, but predominately the 4-isomer.

4-methoxyphenylthiocyanate

NMR (CDCl$_3$) Results: δ($^1$H) 3.76 ppm (s, 3H), 6.89 ppm (d, 2H, J=8.9 Hz), 7.44 ppm (d, 2H, J=8.8 Hz);

$^{13}$C{$^1$H}: 55.26 ppm (s, 1C), 111.39 ppm (s, 1C), 113.41 ppm (s, 1C), 115.59 ppm (s, 2C), 133.49 ppm (s, 2C), 161.02 ppm (s, 1C).

MS (EI) Results: m/e (relative intensity): 165 (M$^+$, 100), 150 (74), 122 (48), 63 (18).

EXAMPLE 2
Thiocyanation of p-xylene 3.5 g (10 mmol) of F-TEDA-BF$_4$ fluorination agent, 0.82 g (10 mmol) of NaSCN, and 100 mL of acetonitrile were added to a 250-mL round bottom flask containing a magnetic stir bar and stirring was commenced. Added to this was 1.1 g (10 mmol) of 1,4-dimethylbenzene (p-xylene) and the contents of the flask were stirred under nitrogen and sampled periodically. After 147 hours of stirring at room temperature, analysis by GC and GC-MS indicated that about 56% conversion of the p-xylene starting material had been achieved with a product distribution of 21% and 26% dimethylphenylthiocyanate derivatives. At this point, the solvent was removed under vacuum on a Rotavap. To the resulting residue was added 200 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 5% ethyl acetate and 95% hexane. Two product fractions were collected, evaporated to residues, and then analyzed separately by NMR spectroscopy and GC-MS. The analysis was consistent with 4-methylbenzylthiocyanate and 2,5-dimethylphenylthiocyanate.

4-methylbenzylthiocyanate

NMR (CDCl$_3$): ($^1$H) 2.34 ppm (s, 3H), 4.13 ppm (s, 2H), 7.20 ppm (m, 4H);

$^{13}$C{$^1$H}: 21.23 ppm (s, 1C), 38.29 ppm (s, 1C), 112.14 ppm (s, 1C), 128.91 ppm (s, 2C), 129.83 ppm (s, 2C), 131.25 ppm (s, 1C), 138.93 ppm (s, 1C);

MS (EI): m/e (relative intensity): 163 (M$^+$, 3), 105 (100), 77 (13).

2,5-dimethylphenylthiocyanate

NMR (CDCl$_3$): ($^1$H) 2.32 ppm (s, 3H), 2.40 ppm (s, 3H), 7.13–7.41 ppm (m, 3H);

$^{13}$C{$^1$H}: 19.80 ppm (s, 1C), 20.72 ppm (s, 1C), 110.61 ppm (s, 1C), 123.05 ppm (s, 1C), 130.95 ppm (s, 1C), 131.16 ppm (s, 1C), 132.20 ppm (s, 1C), 135.99 ppm (s, 1C), 137.69 ppm (s, 1C);

MS m/e (relative intensity): 163 (M$^+$, 100), 135 (85), 105 (21), 77 (33).

EXAMPLE 3
Nitration of Anisole 3.5 g (10 mmol) of F-TEDA-BF$_4$ fluorination agent, 0.69 g (10 mmol) of NaNO$_2$, and 100 mL of acetonitrile were added to a 250-mL round bottom flask containing a magnetic stir bar and stirring was commenced. Added to this was 1.1 g (10 mmol) of anisole and the contents of the flask were stirred under nitrogen and sampled periodically. After 120 hours of stirring at room temperature, analysis by GC and GC-MS indicated that about 43% conversion of the anisole starting material had been achieved with a product distribution of 2% 2-nitroanisole and 4% 4-nitroanisole as nitrated products. The reaction products were purified from the solvent and analyzed as in Example 2. The analysis was consistent with 2-nitroanisole and 4-nitroanisole.

2-Nitroanisole

NMR (CDCl$_3$): ($^1$H) 3.94 ppm (s, 3H), 7.05 ppm (m, 2H), 7.52 ppm (m, 1H);

$^{13}C\{^1H\}$: 56.45 ppm (s, 1C), 113.44 ppm (s, 1C), 120.25 ppm (s, 1C), 125.71 ppm (s, 2C), 134.2 ppm (s, 1C), 139.7 ppm (s, 1C), 153.0 ppm (s, 1C);

MS (EI): m/e (relative intensity) 153 (M$^+$, 57), 123 (32), 106 (93), 92 (67), 77 (100)

4-Nitroanisole.

NMR (CDCl$_3$): ($^1$H) 3.89 ppm (s, 3H), 6.94 ppm (d, 2H, J=9.2 Hz), 8.19 ppm (d, 2H, J=9.2 Hz);

$^{13}C\{^1H\}$: 55.94 ppm (s, 1C), 113.99 ppm (s, 2C), 125.91 ppm (s, 2C), 141.9 ppm (s, 1C), 164.56 ppm (s, 1C);

MS (EI): m/e (relative intensity) 153 (M$^+$, 100), 123 (71), 92 (58), 77 (53).

EXAMPLE 4

Nitration of Phenol 3.5 g (10 mmol) of F-TEDA-BF$_4$ fluorination agent, 1.0 g (15 mmol) of NaNO$_2$, and 80 mL of acetonitrile were added to a 100-mL round bottom flask containing a magnetic stir bar and stirring was commenced. Added to this was 1.0 g (10 mmol) of phenol and the contents of the flask were stirred under nitrogen and sampled periodically. After 68 hours of stirring at room temperature, analysis by GC and GC-MS indicated that about 98% conversion of the phenol starting material had been achieved with a product distribution which included 79% 4-nitrophenol as the major nitrated product. At this point, the solvent was removed under vacuum on a Rotavap. To the resulting residue was added 200 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 50% ethyl acetate and 50% hexane. A single product fraction was collected, evaporated to a residue, and then analyzed by NMR spectroscopy and GC-MS. The analysis was consistent with 4-nitrophenol.

4-Nitrophenol

NMR (CDCl$_3$): ($^1$H) 6.90 ppm (d, 2H, J=9.1 Hz), 8.14 ppm (d, 2H, J=9.1 Hz);

$^{13}C\{^1H\}$: 115.66 ppm (s, 2C), 126.23 ppm (s, 2C), 140.1 ppm (s, 1C), 161.9 ppm (s, 1C);

MS (EI): m/e (relative intensity) 139 (M$^+$, 100), 122 (5), 93 (10), 81 (36).

EXAMPLE 5

Bromination of Phenol 3.5 g (10 mmol) of F-TEDA-BF$_4$ fluorination agent, 1.9 g (19 mmol) of NaBr, and 80 mL of acetonitrile were added to a 100-mL round bottom flask containing a magnetic stir bar and stirring was commenced. Added to this was 1.0 g (10 mmol) of phenol and the contents of the flask were stirred under nitrogen and sampled periodically. After 3 hours of stirring at room temperature, analysis by GC and GC-MS indicated that greater than 98% conversion of the phenol starting material had been achieved and with a product distribution which included mono- and dibromophenol as the major brominated products. At this point, the solvent was removed under vacuum on a Rotavap. To the resulting residue was added to 200 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 20% ethyl acetate and 80% hexane. Three product fractions were collected, evaporated to solid residues, and then analyzed separately by NMR spectroscopy and GC-MS. The analyses were consistent with 2- and 4-bromophenol and 2,6-dibromophenol.

2-bromophenol

NMR (CDCl$_3$): ($^1$H) 6.7 ppm (m, 1H), 7.0 ppm (m, 1H), 7.3 ppm (m, 1H), 7.5 ppm (m, 1H);

$^{13}C\{^1H\}$: 110.04 ppm (s, 1C), 117.16 ppm (s, 1C), 121.81 ppm (s, 1C), 128.95 ppm (s, 1C), 132.27 ppm (s, 1C), 154.49 ppm (s, 1C);

MS (EI): m/e (relative intensity) 174 (99), 172 (M$^+$, 100), 93 (16).

4-bromophenol

NMR (CDCl$_3$): ($^1$H) 6.78 ppm (d, 2H), 7.31 ppm (d, 2H);

$^{13}C\{^1H\}$: 112.47 ppm (s, 1C), 117.13 ppm (s, 2C), 132.24 ppm (s, 2C), 154.56 ppm (s, 1C);

MS (EI): m/e (relative intensity) 174 (103), 172 (M$^+$, 100), 93 (30).

2,6-dibromophenol.

NMR (CDCl$_3$): ($^1$H) 6.68 ppm (t, 1H, J=8.0 Hz), 7.43 ppm (d, 2H, J=8.0 Hz);

$^{13}C\{^1H\}$: 110.0 ppm (s, 2C), 122.0 ppm (s, 1C), 132.0 ppm (s, 2C);

MS (EI): m/e (relative intensity) 254 (100), 252 (189), 250 (M$^+$, 100), 172 (18).

EXAMPLE 6

Bromination of Anisole 3.5 g (10 mmol) of F-TEDA-BF$_4$ fluorination agent, 1.1 g (11 mmol) of NaBr, and 100 mL of acetonitrile were added to a 100-mL round bottom flask containing a magnetic stir bar and stirring was commenced. To this was added 1.1 g (10 mmol) of anisole and the contents of the flask were stirred under nitrogen and sampled periodically. After 75 hours of stirring at room temperature, analysis by GC and GC-MS indicated that about 90% conversion of the anisole starting material had been achieved with a product distribution which included 4-bromoanisole as the major brominated product in about 90% yield.

No further analyses were done.

EXAMPLE 7

Thiocyanation of N,N-Dimethyaniline 3.5 g (10 mmol) of F-TEDA-BF$_4$ fluorination agent, 1.0 g (12 mmol) of NaSCN, and 40 mL of acetonitrile were added to a 100-mL round bottom flask containing a magnetic stir bar and stirring was commenced. To this was added 1.2 g (10 mmol) of N,N-dimethylaniline and the contents of the flask were stirred under nitrogen and sampled periodically. After 27.5 hours of stirring at room temperature, analysis by GC-MS indicated that about 98% conversion of the dimethylaniline starting material had been achieved and with a single dominant product. At this point, the solvent was removed under vacuum on a Rotavap. To the resulting residue was added 200 mL of de-ionized water. This aqueous mixture was extracted with 2×100 mL portions of methylene chloride; the methylene chloride extracts were combined, dried with MgSO$_4$, and evaporated to a product residue. The resulting residue was purified by chromatography on silica gel using a mixture of 40% ethyl acetate and 60% hexane. A single product fraction was collected, evaporated to a yellow oily residue, and then analyzed separately by NMR spectroscopy and GC-MS. The analysis was consistent with N,N-dimethylaniline-4-thiocyanate.

N,N-dimethylaniline-4-thiocyanate

NMR (CDCl$_3$): ($^1$H) 3.00 ppm (s, 6H), 6.65 ppm (d, 2H), 7.41 ppm (d, 2H);

$^{13}C\{^1H\}$: 40.11 ppm (s, 2C), 106.40 ppm (s, 1C), 110.03 ppm (s, 1C), 113.07 ppm (s, 2C), 134.50 ppm (s, 2C), 151.25 ppm (s, 1C);

MS (EI): m/e (relative intensity): 178 (M$^+$, 100), 163 (12), 152 (25), 134(9), 120(4).

EXAMPLE 8
Nitration of Acetanililde 3.5 g (10 mmol) of F-TEDA-BF$_4$ fluorination agent, 1.36 g (20 mmol) of NaNO$_2$, and 40 mL of acetonitrile were added to a 100-mL round bottom flask containing a magnetic stir bar and stirring was commenced. To this was added 1.35 g (10 mmol) of acetanilide and the contents of the flask were stirred under nitrogen and sampled periodically. After 26.5 hours of stirring at room temperature, analysis by GC and GC-MS indicated that about 10% conversion of the acetanilide starting material had been achieved and with a product distribution which included 4-nitroacetanilide as the major nitrated product. At this point, the solvent was removed under vacuum on a Rotavap. To the resulting residue was added 200 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 50% ethyl acetate and 50% hexane. A mixed product fraction was collected, evaporated to a residue, and then analyzed by GC-MS. The fraction contained 2-fluoroacetanilide (26%), acetanilide (27%) and 4-nitro- acetanilide (47%).

4-Nitroacetanilide
MS (EI): m/e (relative intensity) 180 (M$^+$, 14), 138 (100), 134 (11).

EXAMPLE 9
Bromination of Acetanilide 3.5 g (10 mmol) of F-TEDA-BF$_4$ fluorination agent, 1.95 g (19 mmol) of NaBr, and 40 mL of acetonitrile were added to a 100-mL round bottom flask containing a magnetic stir bar and stirring was commenced. To this was added 1.35 g (10 mmol) of acetanilide and the contents of the flask were stirred under nitrogen and sampled periodically. After 3.5 hours of stirring at room temperature, analysis by GC and GC-MS indicated that greater than 98% conversion of the acetanilide starting material had been achieved and with a product distribution which includes 2-monobrominated products. At this point, the solvent was removed under vacuum on a Rotavap. To the resulting residue was added 100 mL of de-ionized water. This aqueous mixture was extracted with 2×100 mL portions of methylene chloride. The methylene chloride extracts were combined, dried with MgSO$_4$, and evaporated to a product residue. The resulting residue was purified by chromatography on silica gel using a mixture of 60% ethyl acetate and 40% hexane. A product fraction was collected and evaporated to a white solid residue. This residue was analyzed by NMR spectroscopy and GC-MS. The analysis of this white solid fraction was consistent with 4-bromoacetanilide.

4-bromoacetanilide
NMR (CDCl$_3$): ($^1$H) 2.14 ppm (s, 3H), 7.0–7.5 ppm (m, 4H);
$^{13}$C{$^1$H}: 14.3 ppm (s, 1C), 117.1 ppm (s, 1C), 121.3 ppm (s, 2C), 131.9 ppm (s, 2C), 138.5 ppm (s, 1C), 168.3 ppm (s, 1C);
MS (EI): m/e (relative intensity) 213 (M$^+$, 20), 171 (100).

EXAMPLE 10
Bromination of Toluene 3.5 g (10 mmol) of F-TEDA-BF$_4$ fluorination agent, 1.03 g (10 mmol) of NaBr, and 100 mL of acetonitrile were added to a 100-mL round bottom flask containing a magnetic stir bar and stirring was commenced. To this was added 0.92 g (10 mmol) of toluene and the contents of the flask were stirred under nitrogen and sampled periodically. After 93.5 hours of stirring at room temperature, analysis by GC and GC-MS indicated that about 35% conversion of the toluene starting material had been achieved with a product distribution which included 2- and 4-bromotoluene and bromomethylbenzene. No further analyses were done.

EXAMPLE 11
Chlorination of Toluene 3.5 g (10 mmol) of F-TEDA-BF$_4$ fluorination agent, 0.60 g (10 mmol) of NaCl, and 100 mL of acetonitrile were added to a 100-mL round bottom flask containing a magnetic stir bar and stirring was commenced. To this was added 0.92 g (10 mmol) of toluene and the contents of the flask were stirred at reflux under nitrogen and sampled periodically. After 47 hours of stirring at reflux, analysis by GC and GC-MS indicated that about 75% conversion of the toluene starting material had been achieved with a product distribution which included 2-chlorotoluene (63%), 4-chlorotoluene (32%), chloromethylbenzene (1%), and fluorotoluene (4%) as the major species. No further analyses were done.

EXAMPLE 12
Chlorination of Acetanilide 3.5 g (10 mmol) of F-TEDA-BF$_4$ fluorination agent, 0.60 g (10 mmol) of NaCl, and 100 mL of acetonitrile were added to a 250-mL round bottom flask containing a magnetic stir bar and stirring was commenced. To this was added 1.35 g (10 mmol) of acetanilide and the contents of the flask are stirred under nitrogen and sampled periodically. After 22.5 hours of stirring at room temperature, analysis by GC and GC-MS indicated that approximately 53% conversion of the acetanilide starting material had been achieved and with a product distribution which include 2-chloroacetanilide (42.7%) and 4-chloroacetanilide (30.0%) as the major chlorinated products. Also observed was chlorofluoroacetanilide (4.9%), fluoroacetanilide (21.9%) and difluoroacetanilide (0.2%).

2-chloroacetanilide
MS (EI): m/e (relative intensity) 169 (M$^+$, 11), 134 (33), 127(100).

chlorofluoroacetanilide
MS (EI): m/e (relative intensity) 187 (M$^+$, 12), 145 (100), 127(3), 110(4).

fluoroacetanilide
MS (EI): m/e (relative intensity) 153 (M$^+$, 17), 111 (100).

EXAMPLE 13
Chlorination of Acetanilide

This is a repeat of Example 12 with the exception of using an excess of F-TEDA-BF$_4$ in order to get complete conversion of the acetanilide starting material. In this experiment, 15.0 g (42 mmol) of F-TEDA-BF$_4$ fluorination agent, 1.17 g (20 mmol) of NaCl, and 200 mL of acetonitrile were added to a 500-mL round bottom flask containing a magnetic stir bar and stirring was commenced. To this was added 2.70 g (20 mmol) of acetanilide and the contents of the flask were stirred under nitrogen and sampled periodically. After 90 hours of stirring at room temperature, analysis by GC and GC-MS indicated that complete conversion of the acetanilide starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with MgSO$_4$, and evaporated to a product residue which weighed 3.49 g. A portion of this residue was dissolved in acetonitrile and analyzed by GC-MS. Analysis indicated a product distribution which included 2-chloroacetanilide (46.3%) and 4-chloroacetanilide (16.2%) as the major chlorinated products. Also observed was chlorofluoroacetanilide (6.6%), fluoroacetanilide (16.2%) and dichloroacetanilide (14.7%).

2-chloroacetanilide
MS (EI): m/e (relative intensity) 169 ($M^+$, 15), 134 (35), 127(100).
chlorofluoroacetanilide
MS (EI): m/e (relative intensity) 187 ($M^+$, 17), 145 (100).
fluoroacetanilide
MS (EI): m/e (relative intensity) 153 ($M^+$, 17), 111 (100).
2,4-dichloroacetanilide
MS (EI): m/e (relative intensity) 203 ($M^+$, 15), 168 (14), 161(100), 133(6).

EXAMPLE 14

Chlorination of p-xylene 15.0 g (42 mmol) of F-TEDA-$BF_4$ fluorination agent, 1.17 g (20 mmol) of NaCl, and 200 mL of acetonitrile were added to a 500-mL round bottom flask containing a magnetic stir bar and stirring was commenced. To this was added 2.13 g (20 mmol) of p-xylene and the contents of the flask are stirred under nitrogen. After 93 hours of stirring at room temperature, analysis by GC and GC-MS indicated that complete conversion of the p-xylene starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with $MgSO_4$, and evaporated to a product residue which weighed 2.02 g. A portion of this residue was dissolved in acetonitrile and analyzed by GC-MS and shown to contain primarily 2-chloro-1,4-dimethylbenzene as well as some dichlorinated and fluorinated products. The product residue was purified by chromatography on silica gel using hexane as the eluent. Two product fractions were collected, evaporated to residues, and then analyzed separately by NMR spectroscopy and GC-MS. The analysis were consistent with 2-chloro-1,4-dimethylbenzene as the primary product in each fraction.

2-chloro-1,4-dimethylbenzene
NMR ($CDCl_3$): ($^1H$) 2.31 ppm (s, 3H), 2.36 ppm (s, 3H), 6.94 –7.18 ppm (m, 3H);
$^{13}C\{^1H\}$: 19.41 ppm (s, 1C), 20.62 ppm (s, 1C), 127.32 ppm (s, 1C), 129.62 ppm (s, 1C), 130.66 ppm (s, 1C), 132.79 ppm (s, 1C), 134.25 ppm (s, 1C), 136.93(s, 1C);
MS (EI): m/e (relative intensity): 140 ($M^+$, 42), 125 (10), 105 (100).

EXAMPLE 15

Chlorination of Anisole 15.0 g (42 mmol) of F-TEDA-$BF_4$ fluorination agent, 1.17g (20 mmol) of NaCl, and 200 mL of acetonitrile were added to a 500-mL round bottom flask containing a magnetic stir bar and stirring was commenced. To this was added 2.16 g (20 mmol) of anisole and the contents of the flask were stirred under nitrogen. After 98 hours of stirring at room temperature, analysis by GC and GC-MS indicated that complete conversion of the anisole starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with $MgSO_4$, and evaporated to a product residue which weighed 2.40 g. A portion of this residue was dissolved in acetonitrile and analyzed by GC-MS and shown to contain primarily 2-chloroanisole (27%) and 4-chloroanisole (18%) as the major chlorinated species, but also contained dichloroanisole (24%), fluoroanisole (18%), chlorofluoroanisole (12%), difluoroanisole (1%), and chlorodifluoroanisole (0.2%) as minor components.

2-chloroanisole
MS (EI): m/e (relative intensity) 142 ($M^+$, 100), 127(51).
4-chloroanisole
MS (EI): m/e (relative intensity) 142 ($M^+$, 100), 127(43).
2,4-dichloroanisole
MS (EI): m/e (relative intensity) 176 ($M^+$, 100), 161(80), 126(4).
chlorofluoroacetanilide
MS (EI): m/e (relative intensity) 187 ($M^+$, 12), 145 (100), 127(3), 110(4).
fluoroacetanilide
MS (EI): m/e (relative intensity) 153 ($M^+$, 17), 111 (100).

EXAMPLE 16

Chlorination of 2-Fluoroanisole 15.0 g (42 mmol) of F-TEDA-$BF_4$ fluorination agent, 1.17 g (20 mmol) of NaCl, and 200 mL of acetonitrile were added to a 500-mL round bottom flask containing a magnetic stir bar and stirring was commenced. To this was added 2.52 g (20 mmol) of 2-fluoroanisole and the contents of the flask were stirred under nitrogen. After 26 hours of stirring at room temperature, analysis by (GC) indicated that approximately 52% conversion of the 2-fluoroanisole starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with $MgSO_4$, and evaporated to a product residue which weighed 2.31 g. A portion of this residue was dissolved in acetone and analyzed by GC-MS and shown to contain chloro-2-fluoroanisole (50%) as the primary chlorinated species, but also contained minor amounts of difluoroanisole (1%) and chloroanisole (1%).

chloro-2-fluoroanisole
MS (EI): m/e (relative intensity) 160 ($M^+$, 100), 145(89).
difluoroanisole
MS (EI): m/e (relative intensity) 144 ($M^+$, 100), 129 (90), 113 (6).

EXAMPLE 17

Chlorination of 4-Fluoroanisole 15.0 g (42 mmol) of F-TEDA-$BF_4$ fluorination agent, 1.18 g (20 mmol) of NaCl, and 200 mL of acetonitrile were added to a 500-mL round bottom flask containing a magnetic stir bar and stirring was commenced. To this was added 2.53 g (20 mmol) of 4-fluoroanisole and the contents of the flask were stirred under nitrogen. After 26 hours of stirring at room temperature, analysis by GC indicated that approximately 53% conversion of the 4-fluoroanisole starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with $MgSO_4$, and evaporated to a product residue which weighed 2.06 g. A portion of this residue was dissolved in acetone and analyzed by GC-MS and shown to contain 2-chloro-4-fluoroanisole (48%) as the primary chlorinated species, but also contained minor amounts of difluoroanisole (3.3%) and chlorofluorophenol derivatives.

2-chloro-4-fluoroanisole
MS (EI): m/e (relative intensity) 160 ($M^+$, 100), 145 (95).

EXAMPLE 18
Chlorination of 2-Chloro-p-Xylene 15.0 g (42 mmol) of F-TEDA-BF$_4$ fluorination agent, 1.18 g (20 mmol) of NaCl, and 200 mL of acetonitrile were added to a 500-mL round bottom flask containing a magnetic stir bar and stirring was commenced. To this was added 2.81 g (20 mmol) of 2-chloro-p-xylene and the contents of the flask are stirred under nitrogen. After 24 hours of stirring at room temperature, analysis by GC indicated that approximately 58% conversion of the 2-chloro-p-xylene starting material had been achieved. At this point, the solvent was removed under vacuum on a Rotavap. To the resulting residue was added 100 mL of de-ionized water. This aqueous mixture was extracted with 3×100 mL portions of chloroform. The chloroform extracts were combined, dried with MgSO$_4$, and evaporated to a product residue which weighed 2.20 g. A portion of this residue was dissolved in acetone and analyzed by GC-MS and shown to contain dichloro-p-xylene (55%) as the primary chlorinated species, but also contained minor amounts (<1%) of chlorofluoro-p-xylene and fluorodichloro-p-xylene.

EXAMPLE 19
Chlorination of Phenol 3.5 g (10 mmol) of F-TEDA-BF$_4$ fluorination agent, 1.0 g (17 mmol) of NaCl, and 80 mL of acetonitrile were added to a 100-mL round bottom flask containing a magnetic stir bar and stirring was commenced. To this was added 1.0 g (10 mmol) of phenol and the contents of the flask are stirred under nitrogen and sampled periodically. Although the analysis did not change much after the initial sample taken at 21 hours of reaction time, the mixture was allowed to stir for an additional 120 hours. After 141 hours of stirring at room temperature, analysis by GC and GC-MS indicated that about 64% conversion of the phenol starting material had been achieved with a product distribution which included 2-chlorophenol (56%) as the major chlorinated product and 2-fluorophenol (44%) as the other major product. Very small amounts of 4-chloro and 4-fluorophenol were also observed.

2-chlorophenol
MS (EI): m/e (relative intensity) 128 (M$^+$, 100), 92(13).
2-fluorophenol
MS (EI): m/e (relative intensity) 112 (M$^+$, 100), 92 (22).

EXAMPLE 20
Thiocyanation of Phenol 3.5 g (10 mmol) of F-TEDA-BF$_4$ fluorination agent, 1.22 g (15 mmol) of NaSCN, and 80 mL of acetonitrile were added to a 100-mL round bottom flask containing a magnetic stir bar and stirring was commenced. To this was added 1.0 g (10 mmol) of phenol and the contents of the flask were stirred under nitrogen and sampled periodically. After 93 hours of stirring at room temperature, analysis by GC-MS indicated that about 21% conversion of the phenol starting material had been achieved. GC-MS analysis showed that ortho-phenolthiocyanate (1%) and para-phenolthiocyanate (20%) were the predominant products.

2-phenolthiocyanate
MS (EI): m/e (relative intensity) 151 (M$^+$, 100), 124 (7).
4-phenolthiocyanate
MS (EI): m/e (relative intensity) 151 (M$^+$, 100), 123 (19).

EXAMPLE 21
Acetylation of p-Xylene 3.5 g (10 mmol) of F-TEDA-BF$_4$ fluorination agent, 0.77 g (10 mmol) of ammonium acetate, NH$_4^+$CH$_3$COO$^-$, and 80 mL of acetonitrile were added to a 100-mL round bottom flask containing a magnetic stir bar and stirring was commenced. To this was added 1.1 g (10 mmol) of p-xylene and the contents of the flask were stirred under nitrogen and sampled periodically. After 70 hours of stirring at room temperature, analysis by GC-MS indicated that about 3% conversion of the p-xylene starting material had been achieved. GC-MS analysis showed a trace amount of the expected ortho substituted product, 2,5-dimethylphenyl acetate.

2,5-dimethylphenyl acetate
MS (EI): m/e (relative intensity) 164 (M$^+$, 12), 122 (100).

EXAMPLE 22
Chlorination of Benzene 3.54 g (10 mmol) of F-TEDA-BF$_4$ fluorination agent, 0.5891 g (10 mmol) of NaCl, and 80 mL of acetonitrile were added to a 100-mL round bottom flask containing a magnetic stir bar and stirring was commenced. To this was added 0.78 g (10 mmol) of benzene and the contents of the flask were stirred under nitrogen and sampled periodically. After 72 hours of stirring at room temperature, analysis by GC-MS indicated that complete conversion of the benzene starting material had been achieved. GC-MS analysis showed a single product which was identified as chlorobenzene.

chlorobenzene
MS (EI): m/e (relative intensity) 112 (M$^+$, 100), 77 (51).

EXAMPLE 23
Bromination of Benzene 3.54 g (10 mmol) of F-TEDA-BF$_4$ fluorination agent, 1.0834 g (11 mmol) of NaBr, and 80 mL of acetonitrile were added to a 100-mL round bottom flask containing a magnetic stir bar and stirring was commenced. To this was added 0.78 g (10 mmol) of benzene and the contents of the flask were stirred under nitrogen and sampled periodically. After 72 hours of stirring at room temperature, analysis by GC-MS indicated that complete conversion of the benzene starting material had been achieved. GC-MS analysis showed a single product which was identified as bromobenzene.

bromobenzene
MS (EI): m/e (relative intensity) 156 (M$^+$, 59), 77 (100).

EXAMPLE 24
Nitration of Benzene

In a typical experiment 3.54 g (10 mmol) of F-TEDA-BF$_4$ fluorination agent, 0.7248 g (11 mmol) of NaNO$_2$, and 80 mL of acetonitrile were added to a 100-mL round bottom flask containing a magnetic stir bar and stirring was commenced. To this was added 0.78 g (10 mmol) of benzene and the contents of the flask were stirred under nitrogen and sampled periodically. After 72 hours of stirring at room temperature, analysis by GC-MS indicated that complete conversion of the benzene starting material had been achieved. GC-MS analysis showed a single product which was identified as nitrobenzene.

nitrobenzene
MS (EI): m/e (relative intensity) 123 (M$^+$, 46), 77 (100).

EXAMPLE 25
Chlorination of 1,3-Dimethyluracil 3.54 g (10 mmol) of F-TEDA-BF$_4$ fluorination agent, 0.58 g (10 mmol) of NaCl, and 80 mL of acetonitrile were added to a 100-mL round bottom flask containing a magnetic stir bar and stirring was commenced. To this was added 0.82 g (6 mmol) of 1,3-dimethyluracil and the contents of the flask were stirred under nitrogen and sampled periodically. After 94 hours of stirring at room temperature, analysis by GC-MS indicated that complete conversion of the 1,3- dimethyluracil starting material had been achieved. GC-MS analysis showed a product distribution which included 5-chloro-6-fluoro-1,3-dimethyluracil (41%) and 5-chloro-1,3-dimethyluracil (24%) as major products.

5-chloro-6-fluoro-1,3-dimethyluracil
MS (EI): m/e (relative intensity) 193 ($M^+$, 100), 174 (1), 158 (8).

5-chloro-1,3-dimethyluracil
MS (EI): m/e (relative intensity) 174 ($M^+$, 100).

EXAMPLE 26
Chlorination of Anisole with Varying Amounts of F-TEDA-$BF_4$

In this experiment, 20, 10, 5, and 1 mmol of F-TEDA-$BF_4$ fluorination agent were weighed, respectively, into 4 individual 250-mL flasks, and to each flask was added 1.17 g (20 mmol) of NaCl, 200 mL of acetonitrile, and 2.2 g (20 mmol) of anisole. A magnetic stir bar was added to each and the contents of the flasks were stirred under nitrogen. Samples from each flask were taken after 46.5 hours and analyzed by GC. The main chlorinated products were 2- and 4-chloroanisole. The results are summarized in Table EG-26 below.

TABLE EG-26

| Amount F-TEDA-$BF_4$ | Anisole Conversion | % 2-chloroanisole | % 4-chloroanisole |
|---|---|---|---|
| 1 mmol | 0% | 0% | 0% |
| 5 mmol | 1% | 0.4% | 0.1% |
| 10 mmol | 42% | 24% | 10% |
| 20 mmol | 75% | 41% | 15% |

EXAMPLE 27
Chlorination of Anisole Using NFTh Fluorination Agent

In this experiment, the ability of NFTh fluorination agent to accomplish the novel generation of electrophilic chlorine from chloride ion was assessed and was compared directly to the same reaction using an equivalent amount of F-TEDA-$BF_4$. Thus, in two separate flasks was weighed 0.58 g NaCl (10 mmol), 1.1 g anisole (10 mmol), and 100 mL acetonitrile. To flask 1 was added 3.5 g (10 mmol) of F-TEDA-$BF_4$ and to the second flask was added 3.2 g (10 mmol) of NFTh. Stirring was commenced and the contents were monitored periodically by GC. After 117 hours the reactions were deemed complete and in Table EG-27 below is an assay of each reaction mixture.

TABLE EG-27

| | Anisole Conversion | % 2-chloroanisole | % 4-chloroanisole |
|---|---|---|---|
| F-TEDA-$BF_4$ | ≈84% | 60% | 20% |
| NFTh | ≈76% | 48% | 15% |

EXAMPLE 28
Chlorination of p-Xylene Using NFTh Fluorination Agent

In this experiment, the ability of NFTh fluorination agent to accomplish the novel generation of electrophilic chlorine from chloride ion was assessed and was compared directly to the same reaction using an equivalent amount of F-TEDA-$BF_4$. Thus, in two separate flasks were weighed 0.58 g NaCl (10 mmol), 1.1 g p-xylene (10 mmol), and 100 mL acetonitrile. To flask 1 was added 3.5 g (10 mmol) of F-TEDA-$BF_4$ and to the second flask was added 3.2 g (10 mmol) of NFTh. Stirring was commenced and the contents were monitored periodically by GC. After 121 hours the reactions were deemed complete the results are shown in Table EG-28 below.

TABLE EG-28

| | p-xylene Conversion | % 2-chloro-p-xylene | % dichloro-p-xylene |
|---|---|---|---|
| F-TEDA-$BF_4$ | ≈74% | 78% | 14% |
| NFTh | ≈54% | 90% | 6% |

EXAMPLE 29
Chlorination of Toluene Using NFTh Fluorination Agent

In this experiment, the ability of NFTh fluorination agent to accomplish the novel generation of electrophilic chlorine from chloride ion was assessed and was compared directly to the same reaction using an equivalent amount of F-TEDA-$BF_4$. Thus, in two separate flasks were weighed 0.58 g NaCl (10 mmol), 0.92 g toluene (10 mmol), and 100 mL acetonitrile. To flask 1 was added 3.5 g (10 mmol) of F-TEDA-$BF_4$ and to the second flask was added 3.2 g (10 mmol) of NFTh. Stirring was commenced and the contents were monitored periodically by GC. After 47.5 hours the reactions were deemed complete. The results are shown in Table EG-29 below.

TABLE EG-29

| | toluene Conversion | % 2-chlorotoluene | % 4-chlorotoluene |
|---|---|---|---|
| F-TEDA-$BF_4$ | ≈75% | 56% | 43% |
| NFTh | ≈5% | 58% | 42% |

EXAMPLE 30
Chlorination of p-Xylene Using F-TEDA-$BF_4$ in Different Solvents In this experiment, the ability of F-TEDA-$BF_4$ fluorination agent to accomplish the novel generation of electrophilic chlorine from chloride ion was assessed in solvents other than acetonitrile. Thus, in three separate flasks were weighed 0.58 g NaCl (10 mmol), 1.1 g p-xylene (10 mmol), and 3.5 g (10 mmol) of F-TEDA-$BF_4$. To the first flask was added 100 mL methanol, to the second 100 mL dimethylformamide (DMF), and to the third flask was added 50 mL water and 50 mL acetonitrile. Stirring was commenced and the contents were monitored periodically by GC. After 47.5 hours the reactions were terminated. The results are shown in Table EG-30 below.

TABLE EG-30

| solvent | p-xylene Conversion | % 2-chloro-p-xylene | % dichloro-p-xylene |
|---|---|---|---|
| methanol | 0% | 0% | 0% |
| DMF | ≈25% | 100% | 0% |
| 50:50 water/ACN | ≈5% | 100% | 0% |

EXAMPLE 31
Chlorination of Anisole Using F-TEDA-$BF_4$ in Different Solvents In this experiment, the ability of F-TEDA-$BF_4$ fluorination agent to accomplish the novel generation of electrophilic chlorine from chloride ion was assessed in solvents other than acetonitrile. Thus, in three separate flasks was weighed 0.58 g NaCl (10 mmol), 1.1 9 anisole (10 mmol), and 3.5 g (10 mmol) of F-TEDA-BF$_4$. To the first flask was added 100 mL methanol, to the second 100 mL dimethyformamide (DMF), and to the third flask was added 50 mL water and 50 mL acetonitrile. Stirring was commenced and the contents were monitored periodically by GC. After 46 hours the reactions were terminated. The results are shown in Table EG-31 below.

TABLE EG-31

| solvent | anisole Conversion | % chloroanisole | % fluoroanisole |
|---|---|---|---|
| methanol | 0% | 0% | 0% |
| DMF | ≈94% | 100% | 0% |
| 50:50 water/ACN | ≈69% | ≈17% | ≈53% |

EXAMPLE 32

Thiocyanation of Various Substrates Using F-TEDA-BF$_4$ in DMF

In this experiment, the ability of F-TEDA-BF$_4$ fluorination agent to accomplish the novel generation of electrophilic SCN$^+$ from thiocyanate ion was assessed for various aromatic substrates in DMF solvent. Thus, in three separate flasks were weighed 0.82 g NaSCN (10 mmol), 3.5 g (10 mmol) of F-TEDA-BF$_4$, and 100 mL dimethyformamide (DMF). To the first flask was added 1.1 g (10 mmol) of anisole, to the second flask was added 0.92 g (10 mmol) toluene, and to the third flask was added 1.1 g (10 mmol) p-xylene. Stirring was commenced and the contents were monitored periodically by GC. After 70 hours the reactions were terminated. The results are shown in Table EG-32 below.

TABLE EG-32

| substrate | substrate Conversion | % SCN product |
|---|---|---|
| anisole | ≈6% | 100% |
| toluene | 0% | 0% |
| p-xylene | 0% | 0% |

EXAMPLE 33

Nitration of Various Substrates Using F-TEDA-BF$_4$ in DMF

In this experiment, the ability of F-TEDA-BF$_4$ fluorination agent to accomplish the novel generation of electrophilic NO$_2^+$ from nitrite ion was assessed for various aromatic substrates in DMF solvent. Thus, in three separate flasks were weighed 0.69 g NaNO$_2$ (10 mmol), 3.5 g (10 mmol) of F-TEDA-BF$_4$, and 100 mL dimethyformamide (DMF). To the first flask was added 1.1 g (10 mmol) of anisole, to the second flask was added 0.92 g (10 mmol) toluene, and to the third flask was added 1.1 g (10 mmol) p-xylene. Stirring was commenced and the contents were monitored periodically by GC. After 95 hours the reactions were terminated and in the Table below is an assay of each reaction mixture.

TABLE EG-33

| substrate | substrate conversion | % NO$_2$ product |
|---|---|---|
| anisole | 0% | 0% |
| toluene | 0% | 0% |
| p-xylene | 0% | 0% |

EXAMPLE 34

Bromination of Various Substrates Using F-TEDA-BF$_4$ in DMF

In this experiment, the ability of F-TEDA-BF$_4$ fluorination agent to accomplish the novel generation of electrophilic Br$^+$ from bromide ion was assessed for various aromatic substrates in DMF solvent. Thus, in three separate flasks were weighed 1.02 g NaBr (10 mmol), 3.5 g (10 mmol) of F-TEDA-BF$_4$, and 100 mL dimethyformamide (DMF). To the first flask was added 1.1 g (10 mmol) of anisole, to the second flask was added 0.92 g (10 mmol) toluene, and to the third flask was added 1.1 g (10 mmol) p-xylene. Stirring was commenced and the contents were monitored periodically by GC. After 45 hours the reactions were terminated. The results are shown in Table EG-34 below.

TABLE EG-34

| substrate | substrate conversion | % Bromo product |
|---|---|---|
| anisole | 95% | 100% |
| toluene | 100% | 100% |
| p-xylene | 100% | 95% |

EXAMPLE 35

Bromination of 4'-Methoxyacetophenone 3.5 g (10 mmol) of F-TEDA-BF$_4$ fluorination agent, 1.03 g (10 mmol) of NaBr, and 80 mL of acetonitrile were added to a 100-mL round-bottomed flask containing a magnetic stir bar and stirring was commenced. To this was added 1.50 g (10 mmol) of 4'-methoxyacetophenone and the contents of the flask were stirred under nitrogen and sampled periodically. After 95 hours of stirring at room temperature, analysis by GC-MS indicated that about 89% conversion of the 4'-methoxyacetophenone starting material had been achieved, with a product distribution of 3'-bromo-4'-methoxyacetophenone (97%), 2,4-dibromo-1-methoxybenzene (2%), and 1-bromo-4-methoxybenzene (1%) as the brominated products. At this point, the solvent was removed under vacuum on a Rotavap. The resulting crude product was treated with 50 mL each of distilled water and saturated sodium bicarbonate. This aqueous mixture was extracted with 2×200 mL portions of dichloromethane. The dichloromethane extracts were combined, dried with MgSO$_4$, and evaporated to a product residue. This residue was subsequently treated with hexane and ethyl acetate and placed in a freezer to facilitate crystal formation. The resulting crystals were analyzed by NMR spectroscopy and GC-MS. The analyses were consistent with 3'-bromo-4'-methoxyacetophenone.

3'-bromo-4'-methoxyacetophenone

NMR (CDCl$_3$): ($^1$H) 2.53 ppm (s, 3H), 3.95 ppm (s, 3H), 6.91 ppm (d, 1H, J=8.6 Hz), 7.89 ppm (m, 1H, $^1$J=8.5 Hz, $^2$J=2.1 Hz), 8.14 ppm (d, 1H, J=2.1 Hz);

$^{13}$C{$^1$H}: 26.30 ppm (s, 1C), 56.46 ppm (s, 1C), 111.04 ppm (s, 1C), 111.82 ppm (s, 1C), 129.46 ppm (s, 1C), 131.20 ppm (s, 1C), 133.83 ppm (s, 1C), 159.54 ppm (s, 1C), 195.61 ppm (s, 1C);

MS (EI): m/z (relative intensity) 230 (39), 228 (M$^+$, 43), 215 (99), 213 (100), 187 (10) 185 (11).

EXAMPLE 36

Thiocyanation of 4'-Methoxyacetophenone 3.5 g (10 mmol) of F-TEDA-BF$_4$ fluorination agent, 0.81 g (10 mmol) of NaSCN, and 80 mL of acetonitrile were added to a 100-mL round-bottomed flask containing a magnetic stir bar and stirring was commenced. To this was added 1.50 g (10 mmol) of 4'-methoxyacetophenone and the contents of the flask were stirred under nitrogen and sampled periodically. After 95 hours of stirring at room temperature, analysis by GC-MS indicated that about 47% conversion of the 4'-methoxyacetophenone starting material had been achieved, with 4'-methoxy-3'-thiocyanatoacetophenone as the single product. At this point, the solvent was removed under vacuum on a Rotavap. The crude product was treated with 50 mL each of distilled water and saturated sodium bicarbonate. This aqueous mixture was extracted with 2×200 mL portions of dichloromethane. The dichloromethane extracts were combined, dried with $MgSO_4$, and evaporated to a product residue. The resulting residue was purified by chromatography on silica gel using a mixture of 40% ethyl acetate and 60% hexane. Eight product fractions were collected and combined. The solvent was evaporated and the resulting product was analyzed by NMR spectroscopy and GC-MS. The analyses were consistent with 4'-methoxy-3'-thiocyanatoacetophenone.

4'-methoxy-3'-thiocyanatoacetophenone

NMR ($CDCl_3$): ($^1H$) 2.57 ppm (s, 3H), 3.99 ppm (s, 3H), 6.98 ppm (d, 1H, J=8.7 Hz), 8.00 ppm (m, 1H, $^1J$=8.6 Hz, $^2J$=2.1 Hz), 8.15 ppm (d, 1H, J=2.1 Hz);

$^{13}C\{^1H\}$: 26.36 ppm (s, 1C), 56.66 ppm (s, 1C), 109.70 ppm (s, 1C), 110.94 ppm (s, 1C), 113.93 ppm (s, 1C), 130.87 ppm (s, 1C), 131.44 ppm (s, 1C), 131.48 ppm (s, 1C), 159.98 ppm (s, 1C), 195.34 ppm (s, 1C);

MS (EI): m/z (relative intensity) 209 (2), 208 (5), 207 ($M^+$, 37), 193 (12), 192 (100), 151 (1), 149 (2).

EXAMPLE 37
Chlorination of 4'-Methoxyacetophenone 3.5 g (10 mmol) of F-TEDA-$BF_4$ fluorination agent, 0.58 g (10 mmol) of NaCl, and 80 mL of acetonitrile were added to a 100-mL round-bottomed flask containing a magnetic stir bar and stirring was commenced. To this was added 1.50 g (10 mmol) of 4'-methoxyacetophenone and the contents of the flask were stirred under nitrogen and sampled periodically. After 95 hours of stirring at room temperature, analysis by GC-MS indicated that about 73% conversion of the 4'-methoxyacetophenone starting material had been achieved, with a product distribution which included 3'-chloro4'-methoxyacetophenone (97%), 1-chloro-4-methoxybenzene (1%), and 1,3-dichloro-2-methoxybenzene (1%) as chlorinated products. At this point, the solvent was removed under vacuum on a Rotavap. The crude product was treated with 50 mL each of distilled water and saturated sodium bicarbonate. This aqueous mixture was extracted with 2×200 mL portions of dichloromethane. The dichloromethane extracts were combined, dried with $MgSO_4$, and evaporated to a product residue. The resulting residue was dissolved in a mixture of ethyl acetate and hexane and placed in a freezer to promote crystallization. The resulting crystals were analyzed by NMR spectroscopy and GC-MS and the results were consistent with 4'-methoxy-3'-thiocyanatoacetophenone as the product.

3'-chloro-4'-methoxyacetophenone

NMR ($CDCl_3$): ($^1H$) 2.54 ppm (s, 3H), 3.95 ppm (s, 3H), 6.95 ppm (d, 1H, J=8.6 Hz), 7.85 ppm (m, 1H, $^1J$=8.5 Hz, $^2J$=2.2 Hz), 7.97 ppm (d, 1H, J=2.2 Hz);

$^{13}C\{^1H\}$: 26.31 ppm (s, 1C), 56.36 ppm (s, 1C), 111.21 ppm (s, 1C), 112.00 ppm (s, 1C), 128.75 ppm (s, 1C), 130.65 ppm (s, 1C), 130.77 ppm (s, 1C), 158.73 ppm (s, 1C), 195.75 ppm (s, 1C);

MS (EI): m/z (relative intensity) 186 (13), 184 ($M^+$, 39), 171 (31), 169 (100), 154 (1(13).

EXAMPLE 38
Nitration of 4-Nitrophenol 3.5 g (10 mmol) of F-TEDA-$BF_4$ fluorination agent, 0.69 g (10 mmol) of $NaNO_2$, and 80 mL of acetonitrile were added to a 100-mL round-bottomed flask containing a magnetic stir bar and stirring was commenced. To this was added 1.40 g (10 mmol) of 4-nitrophenol and the contents of the flask were stirred under nitrogen and sampled periodically. After 20 hours of stirring at room temperature, analysis by GC-MS indicated near complete conversion of the 4-nitrophenol starting material had been achieved, with 2,4-dinitrophenol as the single product. The reaction solution was treated with distilled water and filtered to remove solids. NMR and GC-MS analysis of the resulting solution were consistent with 2,4-dinitrophenol as the product.

2,4-dinitrophenol

MS (EI): m/z (relative intensity) 184 ($M^+$, 100), 154 (38), 138 (2).

EXAMPLE 39
Bromination of Benzoic Acid 3.6 g (10 mmol) of F-TEDA-$BF_4$ fluorination agent, 1.01 g (10 mmol) of NaBr, and 80 mL of acetonitrile were added to a 100-mL round-bottomed flask containing a magnetic stir bar and stirring was commenced. To this was added 1.20 g (10 mmol) of benzoic acid and the contents of the flask were stirred under nitrogen and sampled periodically. After 142 hours of stirring at room temperature, analysis by GC-MS indicated about 8% conversion of the benzoic acid starting material had been achieved, with bromobenzene as the single brominated product.

bromobenzene

MS (EI): m/z (relative intensity) 158 (54), 156 ($M^+$, 57), 77 (100).

EXAMPLE 40
Chlorination of Anisole Using SynFluor™

3.7 g (10 mmol) of SynFluor™ fluorination agent, 0.59 g (10 mmol) of NaCl, and 80 mL of acetonitrile were added to a 100-mL round-bottomed flask containing a magnetic stir bar and stirring was commenced. To this was added 1.08 g (10 mmol) of anisole and the contents of the flask were stirred under nitrogen and sampled periodically. After 163 hours of stirring at room temperature, analysis by GC-MS indicated that about 71% conversion of the anisole starting material had been achieved, yielding a product distribution including 1-chloro-4-methoxybenzene (53%) and 1-chloro-2-methoxybenzene (<1%) as chlorinated products.

EXAMPLE 41
Bromination of Anisole Using SynFluor™

3.7 g (10 mmol) of SynFluor™ fluorination agent, 1.03 g (10 mmol) of NaBr, and 80 mL of acetonitrile were added to a 100-mL round-bottomed flask containing a magnetic stir bar and stirring was commenced. To this was added 1.07 g (10 mmol) of anisole and the contents of the flask were stirred under nitrogen and sampled periodically. After 24 hours of stirring at room temperature, analysis by GC-MS indicated that near complete conversion of the anisole starting material had been achieved, yielding a product distribution including 1-bromo-4-methoxybenzene (70%), 1-bromo-2-methoxybenzene (6%), and 2,4-dibromo-1-methoxybenzene (6%), as brominated products.

EXAMPLE 42
Nitration of Anisole Using SynFluor™

3.7 g (10 mmol) of SynFluor™ fluorination agent, 0.69 g (10 mmol) of $NaNO_2$, and 80 mL of acetonitrile were added to a 100-mL round-bottomed flask containing a magnetic stir bar and stirring was commenced. To this was added 1.09 g (10 mmol) of anisole and the contents of the flask were stirred under nitrogen and sampled periodically. After 164 hours of stirring at room temperature, analysis by GC-MS indicated that a small amount of the anisole starting material had been converted to a mixture of 1-methoxy-2-nitrobenzene and 1-methoxy-4-nitrobenzene.

EXAMPLE 43
Thiocyanation of Anisole Using SynFluor™

3.7 g (10 mmol) of SynFluor™ fluorination agent, 0.81 g (10 mmol) of NaSCN, and 80 mL of acetonitrile were added to a 100-mL round-bottomed flask containing a magnetic stir bar and stirring was commenced. To this was added 1.10 g (10 mmol) of anisole and the contents of the flask were stirred under nitrogen and sampled periodically. After 119 hours of stirring at room temperature, analysis by GC-MS indicated that about 47% conversion of the anisole starting material had been achieved, yielding a product distribution which included 4-methoxyphenylthiocyanate (37%) as the only thiocyanated product.

EXAMPLE 44
Chlorination of p-Xylene Using SynFluor™

3.7 g (10 mmol) of SynFluor™ fluorination agent, 0.58 g (10 mmol) of NaCl, and 80 mL of acetonitrile were added to a 100-mL round-bottomed flask containing a magnetic stir bar and stirring was commenced. To this was added 1.06 g (10 mmol) of p-xylene and the contents of the flask were stirred under nitrogen and sampled periodically. After 113 hours of stirring at room temperature, analysis by GC-MS indicated that about 28% conversion of the p-xylene starting material had been achieved, yielding a product distribution which included 2-chloro-1,4-dimethylbenzene (37%) as the only chlorinated product.

EXAMPLE 45
Bromination of p-Xylene Using SynFluor™

3.7 g (10 mmol) of SynFluor™ fluorination agent, 1.02 g (10 mmol) of NaBr, and 80 mL of acetonitrile were added to a 100-mL round-bottomed flask containing a magnetic stir bar and stirring was commenced. To this was added 1.06 g (10 mmol) of p-xylene and the contents of the flask were stirred under nitrogen and sampled periodically. After 45 hours of stirring at room temperature, analysis by GC-MS indicated that about 95% conversion of the p-xylene starting material had been achieved, yielding a product distribution which included 2-bromo-1,4-dimethylbenzene (39%) and 1-(bromomethyl)-4-methylbenzene (28%) as the main brominated products.

EXAMPLE 46
Trifluoroacetylation of p-Xylene 3.5 g (10 mmol) of F-TEDA-$BF_4$ fluorination agent, 1.4 g (10 mmol) of $Na^+$ $^-OC(O)CF_3$, and 80 mL of acetonitrile were added to a 100-mL round-bottomed flask containing a magnetic stir bar and stirring was commenced. To this was added 1.1 g (10 mmol) of p-xylene and the contents of the flask were stirred under nitrogen and sampled periodically. After 67 hours of stirring at room temperature, analysis by GC-MS indicated that a small amount of the p-xylene starting material had been converted, yielding a product distribution which included 1,4-dimethyl-2-phenyltrifluoroacetate (1%) single trifluoroacetylated product.

1,4-dimethyl-2-phenyltrifluoroacetate

MS (EI): m/z (relative intensity) 218 ($M^+$, 19), 203 (1), 105 (100).

EXAMPLE 47
Chlorination of Anisole in Proprionitrile Solvent 3.5 g (10 mmol) of F-TEDA-$BF_4$ fluorination agent, 0.6 g (10 mmol) of NaCl, and 100 mL of proprionitrile were added to a 100-mL round-bottomed flask containing a magnetic stir bar and stirring was commenced. To this was added 1.1 g (10 mmol) of anisole and the contents of the flask were stirred under nitrogen and sampled periodically. After 115 hours of stirring at room temperature, analysis by GC-MS indicated that a small amount of the anisole starting material had been converted, yielding a product distribution which included 1-chloro-2-methoxybenzene (2%) and 1-chloro-4-methoxybenzene (1%) as the main chlorinated products.

EXAMPLE 48
Chlorination of cis-Cyclooctene 3.5 g (10 mmol) of F-TEDA-$BF_4$ fluorination agent, 0.6 g (10 mmol) of NaCl, and 80 mL of acetonitrile were added to a 100-mL round-bottomed flask containing a magnetic stir bar and stirring was commenced. To this was added 1.1 g (10 mmol) of cis-cyclooctene and the contents of the flask were stirred under nitrogen and sampled periodically. After 94 hours of stirring at room temperature, analysis by GC-MS indicated nearly complete conversion of the cis-cyclooctene starting material, yielding a product distribution which included chlorocyclooctene (1%) as the main chlorine addition product.

chlorocyclooctene

MS (EI): m/z (relative intensity) 146 (3), 144 ($M^+$, 10), 109 (19).

While the invention has been described in detail and with reference to specific examples thereof, it will be apparent to one skilled in the art that various changes and modifications can be made therein without departing from the spirit and scope thereof.

REFERENCES CITED

1. March, J. *Advanced Organic Chemistry*, Wiley: New York, 1985; pp 447–511; and references therein.
2. De La Mare, P. B. D.; Ridd, J. H. *Aromatic Substitution;* Butterworths: London, 1959; and references therein.
3. De La Mare, P. B. D. Electrophilic Halogenation; Cambridge University Press: London, 1976; and references therein.
4. Buehler, C. A.; Pearson, D. E. Survey of Organic Synthesis; Wiley: New York, 1970; and references therein.
5. Lal, G. S.; Pez, G. P.; Syvret, R. G. *Chem. Rev.* 1996, 96(5), 1737.
6. Abushanab, E.; Bindra, A. P.; Lee, D.-Y. *J. Org. Chem.* 1975, 40(23) 3373.
7. Bonesi, S. M.; Erra-Balsells, R. *J. Heterocyclic Chem.* 1997, 34, 877.
8. Araki, S.; Butsugan, Y. *Tetrahedron Lett.* 1984, 25(4), 441.
9. Goldberg, Y.; Alper, H. *J. Org. Chem.* 1993, 58, 3072.
10. Lambert, F. L.; Ellis, W. D.; Parry, R. J. *J. Org. Chem.* 1965, 30, 304.
11. Cookson, R. F.; Richards, A. C. *J. Chem. Soc., Chem. Commun.* 1974, 585.

12. Gershon, H.; McNeil, M. W. *J. Org. Chem.* 1972, 37(25), 4078.
13. Lindsay-Smith, J. R.; McKeer, L. C. *Tetrahedron Lett.* 1983, 24(30), 3117.
14. Lengyel, I.; Cesare, V.; Stephani, R. *Synth. Commun.* 1998, 28(10), 1891.
15. Hirano, M.; Yakabe, S.; Monobe, H.; Morimoto, T. *Can. J. Chem.* 1997, 75, 1905.
16. Effenberger, F.; Kussmaul, U.; Huthmacher, K. *Chem. Ber.* 1979, 112, 1677.
17. Schlama, T.; Gabriel, K.; Gouverneur, V.; Mioskowski, C. *Angew. Chem. Int. Ed. Engl.* 1997, 36(21), 2342.
18. Kakinami, S.; Moriwaki, M.; Tanaka, T.; Fujisaki, S.; Kakinami, T.; Okamoto, T. *J. Chem. Soc., Perkin Trans. 1,* 1990, 897.
19. Carreno, M. C.; Ruano, G.; Sanz, G.; Toledo, M.; Urbano, A. *Tetrahedron Lett.* 1996, 37(23), 4081.
20. Olah, G. A.; Wang, Q.; Sandford, G.; Prakash, G. K. S. *J. Org. Chem.* 1993, 58, 3194.
21. Kajigaeshi, S.; Kakinami, S.; Yamasaki, H.; Fujisaki, S.; Kondo, M.; Okamoto, T. *Chem. Lett.* 1987, 2109.
22. *New Fluorinating Agents in Organic Synthesis;* German, L.; Zemskov, S., Eds.; Springer-Verlag: Berlin, 1989; and references therein.
23. Fieser and Fieser in *Reagents for Organic Synthesis;* Wiley: New York, Vol 1, pg. 1152, 1967.
24. Tamura, Y.; Kwon, S.; Chun, M. W.; Ikeda, M. *J. Heterocycl. Chem.,* 1978, 15, 425.
25. Fieser and Fieser in *Reagents for Organic Synthesis;* Wiley: New York, Vol 1, pg. 1153, 1967.
26. Angus, A. B.; Bacon, R. G. R. *J. Chem. Soc.,* 1958, 774.
27. Bacon, R. G. R.; Guy, R. G. *J. Chem. Soc.,* 1960, 318.
28. Nagamachi, T.; Fourrey, J-L.; Torrence, P. F.; Waters, J. A.; Witkop, B. *J. Med. Chem.* 1974, 17(4), 403.
29. Bruno, M.; Margarita, R.; Parlanti, L.; Piancatelli, G.; Trifoni, M. *Tetrahedron Lett.* 1998, 39, 3847.
30. Takagi, K.; Takachi, H.; Hayama, N. *Chem. Lett.* 1992, 509.
31. Takagi, K.; Takachi, H.; Sasaki, K. *J. Org. Chem.* 1995, 60, 6552.
32. Li, A. L. *Chinese Chem. Lett.* 1991, 2(9), 675.
33. Olah, G. A.; Kuhn, S. J.; Flood, S. H. *J. Am. Chem. Soc.* 1961, 83, 4571.
34. Olah, G. A.; Kuhn, S. J.; Flood, S. H. *J. Am. Chem. Soc.* 1961, 83, 4581.
35. Olah, G. A.; Kuhn, S. J. *J. Am. Chem. Soc.* 1962, 84, 3684.
36. Olah, G. A.; Kuhn, S. J.; Flood, S. H.; Evans, J. C. *J. Am. Chem. Soc.* 1962, 84, 3687.
37. Kuhn, S. J.; Olah, G. A. *J. Am. Chem. Soc.* 1961, 83, 4564.
38. Olah, G. A.; Lin, H. C. *Synthesis,* 1973, 488.
39. Uemura, S.; Toshimitsu, A.; Okano, M. *J. Chem. Soc., Perkin Trans. 1,* 1978, 1076.
40. Zupan, M.; Iskra, J.; Stavber, S. *Tetrahedron Lett.* 1997, 38(35), 6305.
41. Gilicinski, A. G.; Pez, G. P.; Syvret, R. G.; Lal, G. S. *J. Fluorine Chem.* 1992, 59, 157.

What is claimed is:

1. A process for substituting a substituent on a substrate, said process comprising:

reacting a salt comprising an anionic form of said substituent with an electrophilic fluorination agent to provide an electrophile comprising a cationic form of said substituent; and electrophilically substituting said electrophile on said substrate.

2. The process of claim 1, wherein said substituent is chloride, bromide, thiocyanate, nitrite, acetate or trifluoroacetate.

3. The process of claim 2, wherein said substrate is aromatic.

4. The process of claim 2, wherein said substrate is a non-aromatic.

5. The process of claim 2, wherein said substrate is benzene, anisole, 2-fluoroanisole, 4-fluoroanisole, p-xylene, 2-chloro-p-xylene, toluene, phenol, acetanilide, dimethylaniline, 1,3-dimethyluracil, nitrophenol, benzoic acid, 4'-methoxyacetophenone or cis-cyclooctene.

6. The process of claim 1, wherein said substrate is benzene, anisole, 2-fluoroanisole, 4-fluoroanisole, p-xylene, 2-chloro-p-xylene, toluene, phenol, acetanilide, dimethylaniline, 1,3-dimethyluracil, nitrophenol, benzoic acid, 4'-methoxyacetophenone or cis-cyclooctene.

7. The process of claim 1, wherein said salt is an ammonium salt or a sodium salt.

8. The process of claim 1, wherein said electrophilic fluorination agent is a member selected from the group consisting of 1-chloromethyl4-fluoro-1,4-diazoniabicyclo[2.2.2]octane-bis(tetrafluoroborate), 1-fluoro4-hydroxy-1,4-diazoniabicyclo[2.2.2]octane-bis(tetrafluoroborate), 1-fluoro4-methyl-1,4-diazoniabicyclo[2.2.2]octane-bis(tetrafluoroborate), N,N'-difluoro-2,2'bipyridinium bis(tetrafluoroborate) and mixtures thereof.

9. The process of claim 5, wherein said electrophilic fluorination agent is a member selected from the group consisting of 1-chloromethyl-4-fluoro-1,4-diazoniabicyclo[2.2.2]octane-bis(tetrafluoroborate), 1-fluoro-4-hydroxy-1,4-diazoniabicyclo[2.2.2]octane-bis(tetrafluoroborate), 1-fluoro4-methyl-1,4-diazoniabicyclo[2.2.2]octane-bis(tetrafluoroborate), N,N'-difluoro-2,2'bipyridinium bis(tetrafluoroborate) and mixtures thereof.

10. The process of claim 6, wherein said electrophilic fluorination agent is a member selected from the group consisting of 1-chloromethyl4-fluoro-1,4-diazoniabicyclo[2.2.2]octane-bis(tetrafluoroborate), 1-fluoro4-hydroxy-1,4-diazoniabicyclo[2.2.2]octane-bis(tetrafluoroborate), 1-fluoro-4-methyl-1,4-diazoniabicyclo[2.2.2]octane-bis(tetrafluoroborate, N,N'-difluoro-2,2'bipyridinium bis(tetrafluoroborate) and mixtures thereof.

11. The process of claim 1, wherein said electrophilic fluorination agent comprises a bicyclic group.

12. The process of claim 11, wherein said electrophilic fluorination agent is 1-fluoro-4-methyl-1,4-diazoniabicyclo[2.2.2]octane-bis(tetrafluoroborate).

13. The process of claim 1, wherein said electrophilic fluorination agent is an N-F fluorination agent.

14. The process of claim 13, wherein said N-F fluorination agent is N,N'-difluoro-2,2'bipyridinium bis(tetrafluoroborate).

15. The process of claim 1, wherein said process is conducted in a nitrile-containing solvent.

16. The process of claim 15, wherein said nitrile-containing solvent is a member selected from the group consisting of acetonitrile, proprionitrile and mixtures thereof.

17. The process of claim 15, wherein said process is conducted in a 50:50 (v/v) mixture of water and acetonitrile.

18. The process of claim 1, wherein said process is conducted in an amide-containing solvent.

19. The process of claim 18, wherein said amide-containing solvent is dimethylformamide.

20. The process of claim 1, wherein said process is conducted at an ambient temperature and at an ambient pressure.

21. A process for electrophilically substituting an electrophile on a substrate, said process being represented by Equation (1):

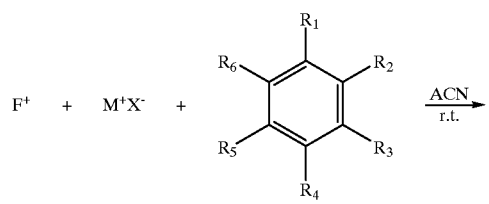
(1)

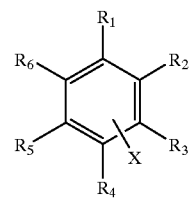

wherein $F^+$ is an electrophilic fluorination agent; $M^+$ is a cation; $X^-$ is chloride, bromide, thiocyanate, nitrite, acetate or trifluoroacetate; and each of $R_{1-6}$ is independently a member selected from the group consisting of H, F, Cl, $CH_3$, COOH, $C(O)CH_3$, $NO_2$, OR' and NR'R", where R' and R" are independently H, $C(O)CH_3$, or $CH_3$.

* * * * *